United States Patent [19]

Watson et al.

[11] 4,417,085

[45] Nov. 22, 1983

[54] PROCESS FOR THE PRODUCTION OF VINYLTOLUENE

[75] Inventors: James M. Watson; Cleve H. Forward; James R. Butler, all of Big Spring, Tex.

[73] Assignee: Cosden Technology, Inc., Dallas, Tex.

[21] Appl. No.: 250,413

[22] Filed: Apr. 2, 1981

[51] Int. Cl.³ ............................................. C07C 5/36
[52] U.S. Cl. .................................... 585/440; 585/441
[58] Field of Search .............................. 585/440, 441

[56] References Cited

U.S. PATENT DOCUMENTS

| | | | |
|---|---|---|---|
| 2,402,740 | 2/1942 | Doumani et al. | 585/440 |
| 2,683,180 | 7/1954 | Amos et al. | 585/440 |
| 3,256,355 | 6/1966 | Gilman et al. | 585/441 |

OTHER PUBLICATIONS

Chem. Engineers' Handbook, Perry and Chilton, 5 Ed. McGraw-Hill (1973) pp. 13-17.

Primary Examiner—Delbert E. Gantz
Assistant Examiner—A. Pal

Attorney, Agent, or Firm—Schwartz, Jeffery, Schwaab, Mack, Blumenthal and Koch

[57] ABSTRACT

A process for the production of vinyltoluene, comprising the steps of: producing a crude vinyltoluene product by the catalytic dehydrogenation of ethyltoluene; removing compounds from the crude vinyltoluene product which have a higher molecular weight than vinyltoluene to form a prepurified crude vinyltoluene product; and fractionally distilling the prepurified crude vinyltoluene product in a distillation apparatus to recover purified vinyltoluene. The higher molecular weight compounds removed are compounds which foster the conversion of vinyltoluene into cross-linked polymer. The compounds removed preferably have more than 11 carbon atoms. In one embodiment, the step of removing higher molecular weight compounds comprises condensing a vaporous crude vinyltoluene product to form a crude vinyltoluene solution, and subjecting the crude vinyltoluene solution to flash distillation to form a vaporous prepurified crude vinyltoluene product. Optionally, the prepurified crude vinyltoluene in the distillation apparatus may include a polymerization inhibitor.

5 Claims, 3 Drawing Figures 4,417,085

PROCESS FOR THE PRODUCTION OF VINYLTOLUENE

BACKGROUND OF THE INVENTION

The present invention pertains to a process for the production of vinyltoluene, and more specifically to a method for inhibiting the formation of undesirable cross-linked thermal polymers in the manufacture of vinyltoluene.

Vinyltoluene is commonly prepared by the catalytic dehydrogenation of ethyltoluene, cooling to condense the gaseous materials and fractionally distilling the liquid product to obtain vinyltoluene.

In processes utilized in the past, the crude vinyltoluene produced by the catalytic dehydrogenation of ethyltoluene has been particularly susceptible to the formation of thermal polymers. When heated, the crude vinyltoluene cross-links to form an insoluble gelatinous polymer. This undesirable byproduct collects in the recycle column and in other parts of the condensation and distillation apparatus, necessitating the cleaning of the column and other equipment, with attendant work stoppage, delay, and expense.

In order to prevent the formation of the thermal polymer during distillation of vinyltoluene, various types of known polymerization inhibitors have been employed in connection with prior art distillation processes. These inhibitors have been only partially effective in preventing the formation of the undesirable thermal polymer in the distillation apparatus. In addition, since the inhibitor is added to the crude vinyltoluene product in the distillation apparatus, the inhibitor does not prevent the formation of the undesirable thermal polymers in the equipment used prior to distillation.

It has been discovered that the removal of hydrocarbons having more than 11 carbon atoms from the crude vinyltoluene greatly increases the time required for the crude vinyltoluene to cross-link, and hence, substantially lowers the amount of polymer formed during vinyltoluene production, particularly in the recycle column.

SUMMARY OF THE INVENTION

It is therefore an object of the present invention to provide an improved process for the production of vinyltoluene.

Another object of the invention resides in the provision of a method for preventing the formation of soluble and insoluble thermal polymers when processing vinyltoluene feed stock prepared by the catalytic dehydrogenation of ethyltoluene.

It is also an object of the present invention to provide an improved process to prevent the fouling of the vinyltoluene production equipment with insoluble thermal polymers, especially the recycle column.

Another object of the invention is to provide for the removal of the high molecular weight compounds from the crude vinyltoluene which accelerate the formation of the undesirable thermal polymers.

A further object of the invention is to provide a new and improved process for the distillation of vinyltoluene which results in higher recovery of high purity vinyltoluene and concomitantly in the production of less undesirable byproducts.

A still further object of the invention resides in the provision of a new and improved process for the distillation of vinyltoluene which results in the production of substantially less polymerized material in the distillation apparatus.

In accomplishing the foregoing objects, there has been provided in accordance with the present invention a process for the production of vinyltoluene comprising the steps of: producing a crude vinyltoluene product by the catalytic dehydrogenation of ethyltoluene; removing compounds from the crude vinyltoluene product which have a higher molecular weight than vinyltoluene to form a prepurified crude vinyltoluene product; and fractionally distilling the prepurified crude vinyltoluene product in a distillation apparatus to recover purified vinyltoluene. The higher molecular weight compounds removed are compounds which foster the conversion of vinyltoluene into cross-linked polymer. The compounds removed preferably have more than 11 carbon atoms. In one embodiment, the step of removing higher molecular weight compounds comprises condensing a vaporous crude vinyltoluene product to form a crude vinyltoluene solution, and subjecting the crude vinyltoluene solution to flash distillation to form a vaporous prepurified crude vinyltoluene product. Optionally, the prepurified crude vinyltoluene in the distillation apparatus may include a polymerization inhibitor.

Through the use of the process according to the present invention, the amount of polymerization occurring before and during the distillation of vinyltoluene is significantly reduced in comparison to conventionally employed methods. In addition, the amount of desired distillation product is increased in proportion to the decrease in the amount of polymer formation.

Other objects, features and advantages of the invention will become apparent from the detailed description of the preferred embodiments which follows, when considered together with the attached figures of drawing.

DETAILED DESCRIPTION OF PREFERRED EMBODIMENTS

Figure 1:
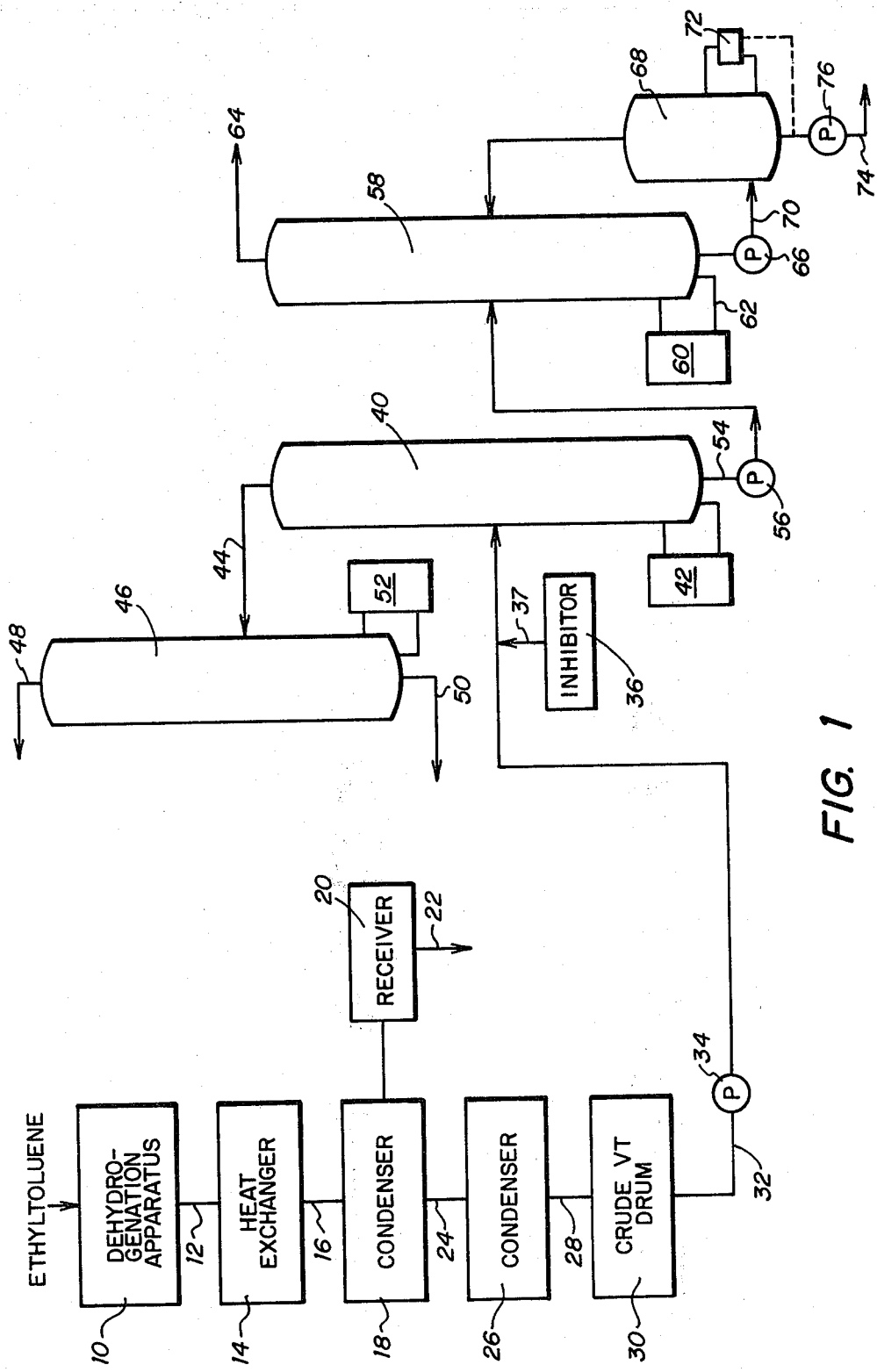
FIG. 1 is a schematic diagram of a preferred embodiment of the apparatus employed in practicing the present invention.

Vinyltoluene is typically manufactured by reacting toluene with ethylene in the presence of an activated Friedel-Crafts catalyst, such as aluminum chloride, or a zeolite catalyst, dehydrogenating the ethyltoluene by passing it together with steam through a dehydrogenation zone at a sufficient reaction temperature, and separating the dehydrogenated product by means of fractional distillation.

The present invention provides a process for the production of vinyltoluene whereby the formation of the undesirable thermal polymer can be greatly inhibited or entirely prevented prior to and during distillation of a vinyltoluene feed stock prepared by the catalytic dehydrogenation of ethyltoluene.

In the process of the invention, the ethylation of toluene is carried out by any suitable conventional process. The ethyltoluenes formed are dehydrogenated by vaporizing the hydrocarbons by means of heat exchangers, passing a stream of vapors into admixture with steam to form a vapor mixture comprising from 1 to 10, advantageously from 2 to 3 parts by weight of steam per part of hydrocarbons, and passing the vapor mixture into a reactor containing a solid, granular dehydrogenation catalyst at reaction temperatures between 550 degrees C. and 700 degrees C., preferably between 560 degrees C. and 650 degrees C. Any of the catalysts which are suitable for use in dehydrogenating ethyltoluene may be used. A considerable number and variety of such catalysts are known and are commercially available. Catalysts of the self-regenerative type are preferred.

A vapor mixture containing steam and vinyltoluene then leaves the dehydrogenation reactor and passes through one or more heat exchangers. The temperature of the vapor mixture is about 345 degrees C. upon leaving the heat exchangers. The vapor mixture is next treated to remove high molecular weight compounds having more than 11 carbon atoms. Such removal may be achieved by any method known to those of skill in the art.

In one embodiment, the vapor mixture is passes into a partial condensing apparatus, where it is cooled to a temperature between about 132 degrees C. and 143 degrees C. The hydrocarbon compounds having more than 11 carbon atoms are selectively condensed and removed. The remaining vaporous crude vinyltoluene product is condensed in a second condenser and collected in a crude vinyltoluene drum. The resulting prepurified crude vinyltoluene product is next transferred from the drum to the distillation apparatus.

In another embodiment, the vaporous crude vinyltoluene product is condensed to form a liquid crude vinyltoluene product. The undesirable high molecular weight compounds are then separated and removed from the vinyltoluene by flashing off the lower boiling fraction having not more than 11 carbon atoms. The lower boiling fraction, constituting a prepurified crude vinyltoluene product, is condensed if desired. The prepurified product is next passed into the distillation apparatus.

A polymerization inhibitor is typically added to the vinyltoluene in the distillation apparatus to prevent any undesirable polymer formation during the distillation of the vinyltoluene. Any of the inhibitors which are suitable for use in preventing the formation of undesirable thermal polymers in vinyltoluene may be used. Suitable inhibitors include the nitrated phenols, such as dinitro-o-cresol, dinitro-p-cresol, m-nitro-p-cresol, dinitrophenol, N-nitroso-diphenylamine, 4-halo-3,5-dinitrotoluene, -3-nitro-2,5-cresotic acid and the like. These inhibitors are employed in amounts ranging generally between about 300–700 ppm. For example, when dinitro-para-cresol (DNPC) is utilized as a polymerization inhibitor, a concentration of about 500 parts DNPC per million by weight relative to the vinyltoluene has been found to be a particularly preferred concentration in preventing the formation of undesirable insoluble polymers during the distillation process.

The dehydrogenation mixture is fractionally distilled in a series of fractionating columns. The distillation is preferably conducted under reduced pressure to further reduce the tendency of the vinyltoluene to polymerize. Lower boiling portions are separated from the vinyltoluene. The vinyltoluene is then removed from the higher boiling fractions. Typical operating conditions for the distillation process include a temperature from about 65 degrees C. to about 138 degrees C., preferably within the range of from about 90 degrees to 115 degrees C., and at a subatmospheric pressure from about 10 to about 200 mm Hg absolute. The specific operating conditions produce a final product of commercial purity vinyltoluene.

Referring to the drawings, FIG. 1 illustrates one embodiment of the present invention. An ethyltoluene feed stock is introduced into a dehydrogenation apparatus 10 to form vinyltoluene. The vaporized crude vinyltoluene flows through line 12 into a heat exchanger 14. Any heat exchanger configuration which will maintain the exit temperature of the vaporized crude vinyltoluene at about 345 degrees C. may be utilized. The vaporized vinyltoluene is transferred from the heat exchanger through line 16 to a partial condensing apparatus 18 where the compounds containing more than 11 carbon atoms are selectively condensed and removed. Any conventional condenser may be used. However, special care must be used to insure that the proper temperature is maintained in the apparatus and thus the desired product is removed. It has been found that by quenching the crude vinyltoluene vapor to about 115 degrees C. to 150 degrees C., and preferably to about 132 degrees to 143 degrees C., removal of the properproduct will result. The product that is condensed in condenser 18 is collected in receiver 20 and removed for proper disposal or further processing via line 22. The product remaining in a vaporous state leaves condenser 18 via line 24 and is condensed in condenser 26. Among the types of condensers suitable for use in the present invention are condensers cooled by air, by water, or by heat cross-exchange with cooler fluids from other stages of the process, or even from other processes.

The condensed product flows through a line 28 to a crude vinyltoluene drum 30. After the product is collected in drum 30, the product is pumped through line 32 via pump 34 into a conventional vinyltoluene distillation train. Preferably, inhibitor 36 is injected by means of line 38 into the crude vinyltoluene feed stock entering the distillation train.

Any conventional distillation train suitable for purifying crude vinyltoluene may be used. In this embodiment, the vinyltoluene feed is introduced into the intermediate portion of recycle column 40 which is preferably of parallel distillation path design. Reboiler 42 provides the necessary heat for distillation in column 40.

An overhead product comprising toluene and ethyltoluene is withdrawn through line 44 for subsequent fractionation in distillation column 46. In column 46, toluene and other light distillates are withdrawn through line 48. An ethyltoluene bottoms product is withdrawn through line 50 and is recycled for use in the ethyltoluene dehydrogenation reactor. Reboiler 52 provides the bottoms with the necessary heat for the distillation.

The recycle bottoms product, containing vinyltoluene, inhibitor, and polyvinyltoluene is withdrawn from the recycle column 40 through line 54 via pump 56 and is charged into the middle portion of finishing column 58. A reboiler circuit comprising a reboiler 60 is attached to the finishing column 58 for supplying the necessary heat within the column. The purified vinyltoluene overhead product is withdrawn through line 64.

The finishing column bottoms product is pumped via pump 66 to flash pot 68 via line 70. The flash pot 68 has a reboiler 72 to facilitate the fractionation of the bottoms. The tar produced during the distillation process is withdrawn through line 74 by pump 76 for proper disposal.

Figure 2:
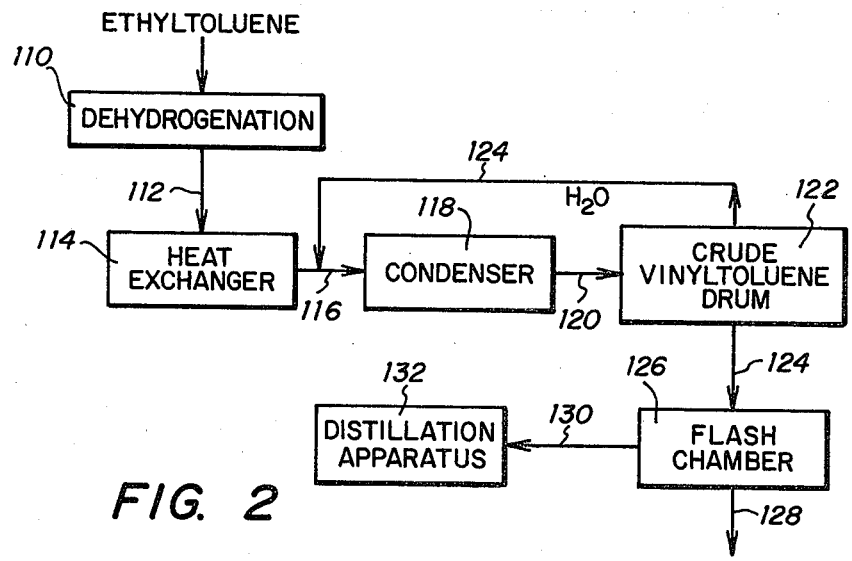
FIG. 2 shows a schematic diagram of another apparatus which may be employed in practicing the invention.

FIG. 2 illustrates another embodiment of an apparatus for carrying out the process of the present invention. An ethyltoluene feed stock is introduced into a dehydrogenation apparatus 110 to form vinyltoluene. Crude vaporous vinyltoluene is transferred through line 112 into heat exchanger 114. Any heat exchanger configuration suitable for cooling the crude vaporous vinyltoluene to an exit temperature of about 345 degrees C. may be used. The crude vaporous vinyltoluene passes from the heat exchanger 114 through line 116 to a condenser 118, where it is condensed to form a liquid crude vinyltoluene. Condenser 118 may be the same as condenser 26 in FIG. 1. The condensed product is transferred through line 120 into crude vinyltoluene drum 122. Preferably, water (from condensed steam) is removed from drum 122 and a portion is pumped through line 124 and introduced into line 116 immediately upstream of condenser 118 to assist in condensing the vaporous crude vinyltoluene.

Liquid crude vinyltoluene is transferred from drum 122 through line 124 into flash chamber 126. Flash chamber 126 may comprise any flash distillation apparatus suitable for separating hydrocarbons having not more than 11 carbon atoms from higher boiling fractions. However, a preferred apparatus contains at least two trays, in order that the lower boiling fraction may more effectively be separated from the compounds having more than eleven carbon atoms. The higher boiling fraction, containing compounds having more than 11 carbon atoms, is removed through line 128 for disposal.

An overhead product, containing lower boiling compounds such as vinyltoluene, toluene, and ethyltoluene, is removed through line 130 and is distilled in a distillation apparatus 130 as discussed in connection with FIG. 1. Any distillation train suitable for producing purified vinyltoluene may be utilized. Though the distillation apparatus illustrated in FIG. 1 first separates a fraction containing toluene and ethyltoluene from vinyltoluene in a recycle column, it is also contemplated to remove an overhead product composed mainly of toluene in a first distillation column, then next to remove an ethyltoluene overhead product from vinyltoluene and heavier impurities in a recycle column. Alternatively, any other sequence of distillation suitable for purifying vinyltoluene may be substituted for the sequences disclosed.

Figure 3:
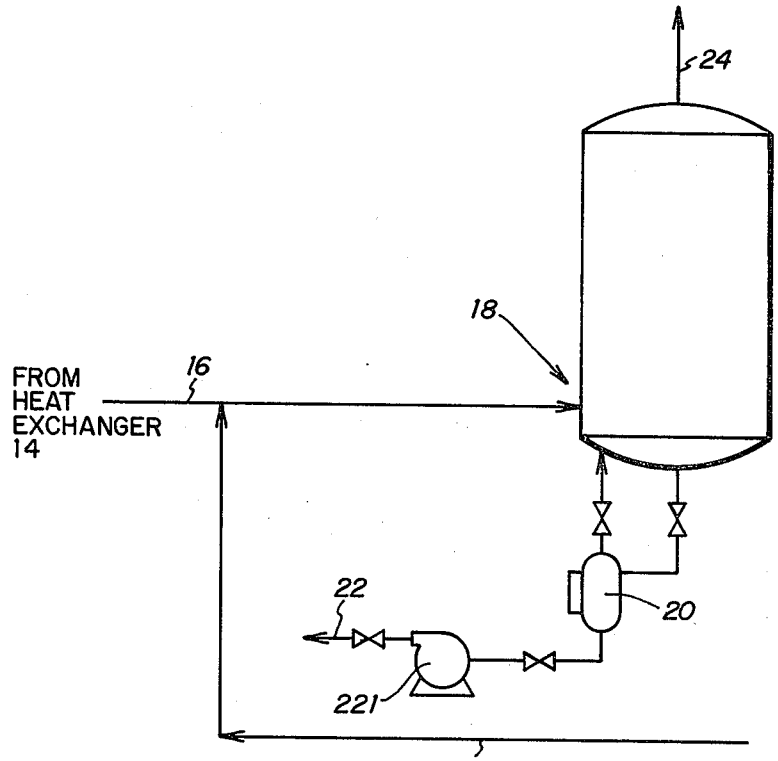
FIG. 3 is a more detailed diagram of the partial condenser for removing higher molecular weight compounds.

FIG. 3 illustrates a preferred embodiment of the partial condenser 18 in FIG. 1. Vaporous crude vinyltoluene exits heat exchanger 14 and is transferred through line 16 at a temperature of about 345 degrees C. Immediately prior to condenser 18, sufficient water is introduced into line 16 from line 227 to lower the temperature of the stream to about 115 degrees C. to 150 degrees C., and preferably to about 132 degrees C. to 143 degrees C. At this temperature, approximately 1% of the vaporous product is condensed, mainly comprising hydrocarbons having more than 11 carbon atoms. The condensed material is collected in receiver 20 and removed for disposal via pump 221 through line 22. The remaining vaporous product is removed through line 24.

Use of the process of the present invention enables an apparatus for the production of vinyltoluene to operate at an increased rate and significantly reduces the amount of unwanted thermal polymer normally formed during the production of vinyltoluene.

The invention will now be further illustrated by the following non-limiting examples.

EXAMPLE 1

Fourteen samples of crude vinyltoluene were placed in an oven at 110 degrees C. Two samples were removed after 5 hours. Two additional samples were removed at each of 7, 9, 11, 13, 15 and 17 hours. The 5, 7 and 9 hour samples dissolved in toluene. The 11, 13 and 15 hour samples did not, indicating that the samples were cross-linked.

EXAMPLE 2

A sample of crude vinyltoluene was flashed in a rotary evaporator at 20 mm/Hg. and at 90 degrees C. The overhead product was condensed and a sample was taken. The above procedure was repeated for second and third successive flashes. There was a 1.39% residue remaining after the first flash, 0.69% after the second flash, and 0.87% after the third flash.

Vinyltoluene samples of the distillate of each of the three successive flashes were placed in an oven at 110 degrees C., as in Example 1, and were examined periodically. Viscosity and solubility of the samples were periodically observed to determine the onset of cross-linking.

After 18.5 hours, the product of the first flash was in the initial stages of cross-linking. It was viscous, but made a fluid mixture with toluene. After 29 hours, the product of the first flash was a clear gel, insoluble in toluene.

The distillate of the second flash flowed well even when cold after 18.5 hours, and was soluble in toluene. After 29 hours, the sample was viscous when hot. A small portion would not dissolve in toluene, indicating the onset of cross-linking. After 46 hours, the sample was stringy and sticky. Much of the sample was soluble in toluene, but a moderate portion would not dissolve.

The distillate of the third flash remained soluble and liquid at 18.5 and 29 hours. After 46 hours, the sample was stringy and would not flow. Most of the sample dissolved in toluene, though a small amount remained insoluble. The sample appeared to be in the initial stages of cross-linking.

An analysis of the distillate of the third flash showed very little change in the concentration of compounds having 11 or fewer carbon atoms (diethyltoluene, etc.). The above data indicate that removal of compounds having more than 11 carbon atoms from crude vinyltoluene significantly prolongs the time necessary for the onset of formation of cross-linked polymer.

EXAMPLE 3

A partial condenser comprising a cylindrical vessel 8' in diameter and 28' in height was installed in the transfer line leading from the effluent heat exchangers to the primary crude vinyltoluene condenser of a commercial vinyltoluene production apparatus to form an apparatus substantially as illustrated in FIG. 1. Sufficient quench water was injected into the transfer line immediately prior to the partial condenser to lower the temperature of the vaporous stream to 134 degrees C. This temperature was sufficient to effect the condensation of approximately 1 weight percent of the organic stream, and in so doing to selectively remove the majority of the organic components having more than 11 carbon atoms from the vapor phase.

The practical effect of the installation of the aforementioned partial condenser has been a dramatic decrease in the fouling of downstream processing equipment with cross-linked polymer during vinyltoluene production.

What is claimed is:

1. A process for the production of vinyltoluene, comprising the steps of:

producing a crude vinyltoluene product by the catalytic dehydrogenation of ethyltoluene;

selectively removing hydrocarbon compounds from the vinyltoluene product which have more than 11 carbon atoms and which foster the conversion of vinyltoluene into cross-linked polymer to form a prepurified crude vinyltoluene product, the hydrocarbon compounds selectively removed by subjecting the crude vinyltoluene product to flash distillation to form a vaporous prepurified crude vinyltoluene product;

and fractionally distilling said prepurified crude vinyltoluene product in a distillation apparatus to recover purified vinyltoluene.

2. A process as claimed in claim 1, wherein the step of removing higher molecular weight compounds comprises condensing a vaporous crude vinyltoluene produce to form a crude vinyltoluene solution, and subjecting said crude vinyltoluene solution to flash distillation to form a vaporous prepurified crude vinyltoluene product.

3. A process as claimed in claim 1, wherein the prepurified crude vinyltoluene in the distillation apparatus includes a polymerization inhibitor.

4. A process as claimed in claim 1, wherein said flash distillation step comprises a plurality of stages.

5. A process as claimed in claim 1, further comprising the step of condensing the vaporous prepurified vinyltoluene product prior to the fractional distillation step.

* * * * *